United States Patent
Yan et al.

(10) Patent No.: US 12,040,070 B2
(45) Date of Patent: Jul. 16, 2024

(54) RADIOTHERAPY SYSTEM, DATA PROCESSING METHOD AND STORAGE MEDIUM

(71) Applicant: CyberMed Radiotherapy Technologies Co., Ltd., Shaanxi (CN)

(72) Inventors: Hao Yan, Shaanxi (CN); Jiuliang Li, Shaanxi (CN); Jinsheng Li, Shaanxi (CN); Peng Zan, Shaanxi (CN); Haifeng Liu, Shaanxi (CN)

(73) Assignee: OUR UNITED CORPORATION, Shaanxi (CN)

( * ) Notice: Subject to any disclaimer, the term of this patent is extended or adjusted under 35 U.S.C. 154(b) by 1256 days.

(21) Appl. No.: 16/093,894

(22) PCT Filed: Jun. 5, 2017

(86) PCT No.: PCT/CN2017/087183
§ 371 (c)(1),
(2) Date: Oct. 15, 2018

(87) PCT Pub. No.: WO2018/223261
PCT Pub. Date: Dec. 13, 2018

(65) Prior Publication Data
US 2020/0185079 A1    Jun. 11, 2020

(51) Int. Cl.
 G16H 20/40  (2018.01)
 G06F 16/23  (2019.01)
 G06N 20/00  (2019.01)

(52) U.S. Cl.
 CPC ......... *G16H 20/40* (2018.01); *G06F 16/2365* (2019.01); *G06N 20/00* (2019.01)

(58) Field of Classification Search
 None
 See application file for complete search history.

(56) References Cited

U.S. PATENT DOCUMENTS 9,409,039 B2   8/2016 Hartman et al.
9,818,406 B1 * 11/2017 Chan .................. G10L 25/63
(Continued)

FOREIGN PATENT DOCUMENTS

CN   101536006 A   9/2009
CN   101820827 A   9/2010
(Continued)

OTHER PUBLICATIONS

China National Intellectual Property Administration, First office action of Chinese application No. 201780003947.X dated Nov. 5, 2019, which is foreign counterpart application of this US application.

(Continued)

*Primary Examiner* — Rajesh Khattar
*Assistant Examiner* — Andrew E Lee
(74) *Attorney, Agent, or Firm* — Daniel J. Chalker; Edwin S. Flores; Chalker Flores, LLP

(57) ABSTRACT

There is provided a radiotherapy system, a data processing method and a storage medium. The radiotherapy system includes a calibration database, a training module and a data processing module. The calibration database can acquire a plurality of the sample data generated in a clinical therapy process. The training module can perform deep learning on the plurality of sample data stored in the calibration database to obtain a therapy algorithm model. The data processing module can process the detection data received in the clinical therapy process according to the therapy algorithm model to generate preliminary therapy data. As the therapy algorithm model is obtained by performing deep learning on a large amount of clinical data, the reliability of the therapy algorithm model is high. Accordingly, the accuracy of the preliminary therapy data generated by the therapy algorithm model is also high.

16 Claims, 3 Drawing Sheets

(56) References Cited

U.S. PATENT DOCUMENTS

| | | | |
|---|---|---|---|
| 2005/0169536 A1* | 8/2005 | Accomazzi | G06V 10/7557 |
| | | | 382/128 |
| 2009/0110145 A1 | 4/2009 | Lu et al. | |
| 2012/0014507 A1 | 1/2012 | Wu et al. | |
| 2014/0350863 A1* | 11/2014 | Hartman | G16H 40/63 |
| | | | 702/19 |
| 2016/0230227 A1 | 8/2016 | Sproul et al. | |
| 2017/0182362 A1* | 6/2017 | McLeod | A61B 5/681 |
| 2018/0137941 A1 | 5/2018 | Chen | |
| 2018/0272153 A1* | 9/2018 | Berlinger | A61N 5/1075 |
| 2018/0300790 A1* | 10/2018 | Dhurandhar | G06Q 30/0631 |
| 2018/0350075 A1* | 12/2018 | Grimmer | G06T 7/40 |
| 2019/0192880 A1* | 6/2019 | Hibbard | A61N 5/1039 |

FOREIGN PATENT DOCUMENTS

| | | |
|---|---|---|
| CN | 102306239 A | 1/2012 |
| CN | 104866727 A | 8/2015 |
| CN | 104881568 A | 9/2015 |
| CN | 105120955 A | 12/2015 |
| CN | 105893772 A | 8/2016 |
| CN | 106529177 A | 3/2017 |
| CN | 106650830 A | 5/2017 |
| CN | 106659906 A | 5/2017 |
| CN | 106777953 A | 5/2017 |
| CN | 101268476 A | 9/2018 |
| WO | 2015081086 A1 | 6/2015 |

OTHER PUBLICATIONS

China National Intellectual Property Administration, Second office action of Chinese application No. 201780003947.X dated May 18, 2020, which is foreign counterpart application of this US application.

China National Intellectual Property Administration, Third office action of Chinese application No. 201780003947.X dated Oct. 19, 2020, which is foreign counterpart application of this US application.

China National Intellectual Property Administration, Decision of rejection of Chinese application No. 201780003947.X dated Mar. 5, 2021, which is foreign counterpart application of this US application.

Haiying Dong Eds., Intelligent Control Theories and Applications, "Deep Learning," Beijing: Trail Press, China, Sep. 30, 2016, pp. 181-183.

Pengcheng Wei et al, Integration and Development of Big Data Macro Analytics and Machine Learning, "4.5.4 Medical Image Processing", pp. 139-140, Chengdu: University of Electronic Science and Technology Press, May 2017.

China National Intellectual Property Administration, First office section of Chinese application No.: 202210303766.1 issued on Apr. 25, 2024, which is foreign counterpart application of the US application.

* cited by examiner

RADIOTHERAPY SYSTEM, DATA PROCESSING METHOD AND STORAGE MEDIUM

CROSS-REFERENCE TO RELATED APPLICATIONS

This application is a U.S. National Stage Application of and claims priority to International Application No. PCT/CN2017/087183, filed on Jun. 5, 2017, the contents of which are incorporated by reference herein in their entirety.

FIELD OF THE INVENTION

The present disclosure relates to the field of radiotherapy technology, and more particularly, to a radiotherapy system, a data processing method and a storage medium.

BACKGROUND OF THE INVENTION

Radiation therapy (RT) is a local therapy method that uses radioactive rays to treat tumors. The modern radiotherapy technology relies increasingly on image information, so that gradually, a new radiotherapy treatment based on a radiotherapy image is formed, such as an imaging guided radiation therapy (IGRT) treatment and an adaptive radiation therapy (ART) treatment.

In the related art, a radiotherapy image-based radiotherapy system mainly comprises a medical image acquisition module, a registration module, a delineation module and a therapy plan generation module. The medical image acquisition module, which may include a computed tomography (CT) equipment, a cone-beam CT equipment, a magnetic resonance imaging (MRI) equipment and the like, is mainly used to acquire lesion images at different therapy stages. The registration module is mainly used to register the lesion images acquired in different ways and stages. The delineation module is mainly used to delineate a tumor area to be irradiated (i.e., a target area) and surrounding vital organs. The therapy plan generation module is mainly used to generate a preliminary therapy plan according to the acquired lesion images and the delineated result.

However, in the radiotherapy system in the related art, data processing modules such as the registration module, the delineation module and the therapy plan generation module generally performs preliminarily processing on the acquired detection data according to a preset model. However, the processing result cannot be used in clinical therapy until all levels of radiotherapy clinicians adjust, confirm and approve the accuracy of the processing result, which takes a lot of time. This process is highly dependent on the professional experience and quality of the radiotherapy clinicians at all levels. Thus, the treatment effect of the current radiotherapy system varies greatly among different hospitals. In addition, due to a large amount of manual intervention, the efficiency needs to be improved.

SUMMARY

There are provided a radiotherapy system, a data processing method and a storage medium.

In a first aspect, there is provided a radiotherapy system comprising:

a calibration database, a training module and a data processing module.

The calibration database is configured to acquire a plurality of sample data generated in a clinical therapy process, where each sample data includes a set of detection data and a set of therapy data corresponding to the set of detection data and applied to clinical therapy.

The training module is configured to perform deep learning on the plurality of sample data stored in the calibration database to obtain a therapy algorithm model, and send the therapy algorithm model to the data processing module.

The data processing module is configured to process the detection data acquired in the clinical therapy process according to the therapy algorithm model to generate preliminary therapy data.

Optionally, the calibration database is further configured to receive modified sample data, where the modified sample data includes modified data for the preliminary therapy data, and detection data corresponding to the preliminary therapy data where the modified data is data actually used for the clinical therapy and obtained after the clinicians modifying the preliminary therapy data.

The training module is further configured to set a weight value of the modified sample data to be greater than a preset weight value, and perform deep learning on updated sample data in the calibration database.

Optionally, the training module is further configured to receive a feedback level of specified sample data, where the feedback level is positively related to a therapeutic effect of the therapy data in the specified sample data.

The training module is further configured to adjust a weight value of the specified sample data according to the feedback level of the specified sample data, and perform deep learning on the sample data with an adjusted weight value in the calibration database, where the adjusted weight value of the specified sample data is positively related to the feedback level of the specified sample data.

Optionally, the radiotherapy system further includes: a communication module configured to send the therapy algorithm model to a cloud server, so that the cloud server sends the therapy algorithm model to local servers of other hospitals.

Alternatively, the radiotherapy system is deployed in the cloud server; the plurality of sample data stored in the calibration database is acquired from a clinical database of a specified hospital; and the communication module is configured to send the therapy algorithm model to a local server of any hospital.

Optionally, the data processing module is configured to receive detection data sent from the local server of any hospital, process the detection data according to the therapy algorithm model to generate the preliminary therapy data, and send the preliminary therapy to the local server.

Optionally, the clinical therapy process includes an image registration stage. The sample data generated at the image registration stage includes a plurality of medical image data and a corresponding registration image. The training module is configured to perform deep learning on the plurality of the sample data generated at the image registration stage to obtain a registration model.

Alternatively, the clinical therapy process includes a delineation stage. The sample data generated at the delineation stage includes a registration image and a corresponding delineation result image. The training module is configured to perform deep learning on the plurality of the sample data generated at the delineation stage to obtain a delineation model.

Alternatively, the clinical therapy process includes a therapy plan formulation stage. The sample data generated at the therapy plan formulation stage includes medical image data, a delineation result image and a corresponding therapy plan. The training module is configured to perform deep learning on the plurality of the sample data generated at the therapy plan formulation stage to obtain a therapy plan formulation model.

Optionally, the clinical therapy process includes a pre-therapy positioning stage. The sample data generated at the pre-therapy positioning stage includes a plurality of medical image data and a corresponding positioning offset. The training module is configured to perform deep learning on the plurality of the sample data generated at the pre-therapy positioning stage to obtain a pre-therapy positioning model.

Alternatively, the clinical therapy process includes an in-therapy monitoring stage. The sample data generated at the in-therapy monitoring stage includes monitoring data and corresponding adjustment data. The monitoring data includes a patient displacement, a tumor monitoring image and a remaining radiation dosage. The adjustment data includes a therapy muzzle displacement, a tumor displacement and a dosage error. The training module is configured to perform deep learning on the plurality of the sample data generated at the in-therapy monitoring stage to obtain a monitoring model.

Optionally, each sample data further includes a set of additional data, and the set of additional data may include at least one piece of patient attribute information.

Data received by the data processing module in the clinical therapy process further includes additional data corresponding to the detection data. The data processing module is further configured to process the received detection data and the corresponding additional data according to the therapy algorithm model to generate the preliminary therapy data.

Optionally, each sample data further includes a set of additional data, and the set of additional data may include at least one piece of patient attribute information.

The calibration database is further configured to classify the plurality of sample data according to content of target patient attribute information in the additional data of each sample data, where the target patient attribute information is determined from the at least one patient attribute information.

The training module is configured to perform deep learning on each classification of sample data stored in the calibration database to obtain multiple classifications of therapy algorithm models.

The data received by the data processing module in the clinical therapy process further includes additional data corresponding to the detection data. The data processing module is further configured to determine a corresponding therapy algorithm model from the multiple classifications of therapy algorithm models according to the content of the target patient attribute information in the additional data, and process the received detection data according to the corresponding therapy algorithm model to generate the preliminary therapy data.

In a second aspect, there is provided a data processing method applied to the radiotherapy system shown in the first aspect. The method includes:

acquiring a plurality of the sample data generated in a clinical therapy process, where each sample data includes a set of detection data and a set of therapy data corresponding to the set of detection data and applied to clinical therapy;

performing deep learning on the plurality of sample data stored in the calibration database to obtain a therapy algorithm model; and processing the detection data acquired in the clinical therapy process according to the therapy algorithm model to generate preliminary therapy data.

Optionally, the method further includes:

receiving modified sample data, where the modified sample data includes modified data for the preliminary therapy data, and detection data corresponding to the preliminary therapy data, where the modified data is the data actually used in the clinical therapy and obtained after the clinicians modifying the preliminary therapy data:

setting a weight value of the modified sample data to be greater than a preset weight value: and performing deep learning on updated sample data in the calibration database.

Optionally, the method further includes:

receiving a feedback level of specified sample data, where the feedback level is positively related to a therapeutic effect of the therapy data in the specified sample data;

adjusting a weight value of the specified sample data according to the feedback level of the specified sample data, where the adjusted weight value of the specified sample data is positively related to the feedback level of the specified sample data; and performing deep learning on the sample data with the adjusted weight value.

Optionally, after obtaining the therapy algorithm model, the method further includes: sending the therapy algorithm model to a cloud server, so that the cloud server sends the therapy algorithm model to local servers of other hospitals.

Alternatively, the radiotherapy system is deployed in a cloud server. The acquiring the plurality of the sample data generated in the clinical therapy process includes: acquiring the plurality of sample data from a clinical database of a specified hospital. After obtaining the therapy algorithm model, the method further includes: sending the therapy algorithm model to a local server of any hospital.

Optionally, the processing the detection data received in the clinical therapy process according to the therapy algorithm model to generate the preliminary therapy data includes: receiving detection data sent from the local server of any hospital; and processing the detection data according to the therapy algorithm model to generate the preliminary therapy data. The method further includes: sending the preliminary therapy to the local server.

Optionally, the clinical therapy process includes an image registration stage. The sample data generated at the image registration stage includes a plurality of medical image data and a corresponding registration image. The performing deep learning on the plurality of sample data stored in the calibration database includes: performing deep learning on the plurality of the sample data generated at the image registration stage to obtain a registration model.

Alternatively, the clinical therapy process includes a delineation stage. The sample data generated at the delineation stage includes a registration image and a corresponding delineation result image. The performing deep learning on the plurality of sample data stored in the calibration database to obtain the therapy algorithm model includes: performing deep learning on the plurality of the sample data generated at the delineation stage to obtain a delineation model.

Alternatively, the clinical therapy process includes a therapy plan formulation stage. The sample data generated at the therapy plan formulation stage includes medical image data, a delineation result image and a corresponding therapy plan. The performing deep learning on the plurality of sample data stored in the calibration database to obtain the therapy algorithm model includes: performing deep learning on the sample data generated at the therapy plan formulation stage to obtain a therapy plan formulation model.

Optionally, the clinical therapy process includes a pre-therapy positioning stage. The sample data generated at the pre-therapy positioning stage includes a plurality of medical image data and a corresponding positioning offset. The performing deep learning on the plurality of sample data stored in the calibration database to obtain the therapy algorithm model includes: performing deep learning on the plurality of the sample data generated at the pre-therapy positioning stage to obtain a pre-therapy positioning model.

Alternatively, the clinical therapy process includes an in-therapy monitoring stage. The sample data generated at the in-therapy monitoring stage includes monitoring data and corresponding adjustment data. The monitoring data includes a patient displacement, a tumor monitoring image and a remaining radiation dosage. The adjustment data includes a therapy gun muzzle displacement, a tumor displacement and a dosage error. Performing deep learning on the plurality of sample data stored in the calibration database to obtain the therapy algorithm model includes: performing deep learning on the plurality of the sample data generated at the in-therapy monitoring stage to obtain a monitoring model.

Optionally, each sample data further includes a set of additional data, and the set of additional data may include at least one piece of patient attribute information.

Data received in the clinical therapy process further includes additional data corresponding to the detection data. The processing the detection data received in the clinical therapy process according to the therapy algorithm model to generate the preliminary therapy data includes:

processing the received detection data and the corresponding additional data according to the therapy algorithm model to generate the preliminary therapy data.

Optionally, each sample data further includes a set of additional data, and the set of additional data may include at least one piece of patient attribute information.

The method further includes: classifying the plurality of sample data according to the content of target patient attribute information in the additional data of each sample data, where the target patient attribute information is determined from the at least one patient attribute information.

The performing deep learning on the plurality of sample data stored in the calibration database to obtain the therapy algorithm model includes:

performing deep learning on each classification of sample data stored in the calibration database to obtain multiple classifications of therapy algorithm models.

Data received in the clinical therapy process further includes additional data corresponding to the detection data. The processing the detection data received in the clinical therapy process according to the therapy algorithm model to generate the preliminary therapy data includes:

determining a corresponding therapy algorithm model from the multiple classifications of therapy algorithm models according to the content of the target patient attribute information in the additional data; and processing the received detection data according to the corresponding therapy algorithm model to generate the preliminary therapy data.

In a third aspect, there is provided a computer-readable storage medium. Instructions are stored in the computer-readable storage medium. When the computer-readable storage medium runs on a computer, the computer executes the data processing method provided by the second aspect.

BRIEF DESCRIPTION OF THE DRAWINGS

In order to more clearly illustrate the technical solutions of the embodiments provided by the present disclosure, a brief introduction may be introduced hereinafter to the drawings that may be used in the description of the embodiments. Apparently, the drawings in the description below are merely for illustrating some embodiments of the present invention, and other drawings may be obtained by those skilled in the art according to these drawings without any creative labor.

The specific embodiments of the present disclosure are shown through the above drawings, and will be described in more detail below. These drawings and textual descriptions are used to illustrate the concept of the present disclosure to those skilled in the art by reference to the specific embodiments, rather than limiting the inventive concept scope of the present disclosure by any means.

DETAILED DESCRIPTION OF THE EMBODIMENTS

To make the objectives, technical solutions and advantages of the present disclosure clearer, the followings will describe the embodiments of the present disclosure in detail with reference to the drawings.

Figure 1:
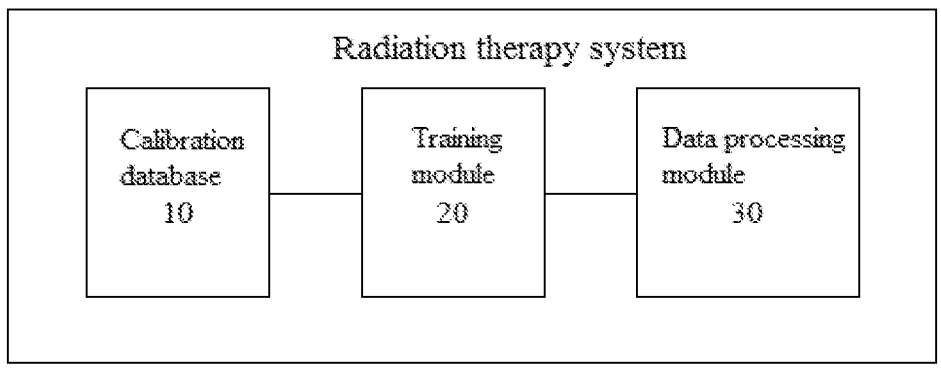
FIG. 1 is a schematic view of a structure of a radiotherapy system provided by an embodiment of the present disclosure.

FIG. 1 is a schematic view of a structure of a radiotherapy system provided by an embodiment of the present disclosure. Specifically, referring to FIG. 1, the system may include: a calibration database 10, a training module 20 and a data processing module 30.

The calibration database 10 may be used to acquire a plurality of the sample data generated in a clinical therapy process, where each sample data comprises a set of detection data, and a set of therapy data corresponding to the set of detection data and applied for clinical therapy.

The calibration database 10 may be accessed to a clinical database of a hospital through a preset database interface. The clinical database may store detection data and therapy data of a plurality of patients. Each patient has a set of detection data and a set of therapy data. The therapy data of each patient is the data verified by clinicians in a therapy process and actually used in the clinical therapy, so the reliability of the therapy data is high. In addition, the amount of calibrated sample data required for deep learning is large, however, the sample data, which is generated in the clinical therapy process, can be acquired directly without any manual calibration, thereby effectively reducing the acquisition difficulty of the sample data.

In the embodiment of the present disclosure, the calibration database 10 may acquire the detection data and the therapy data corresponding to the detection data from the clinical database in real time or periodically, and can store each set of detection data and the set of corresponding therapy data as one sample data.

Figure 2:
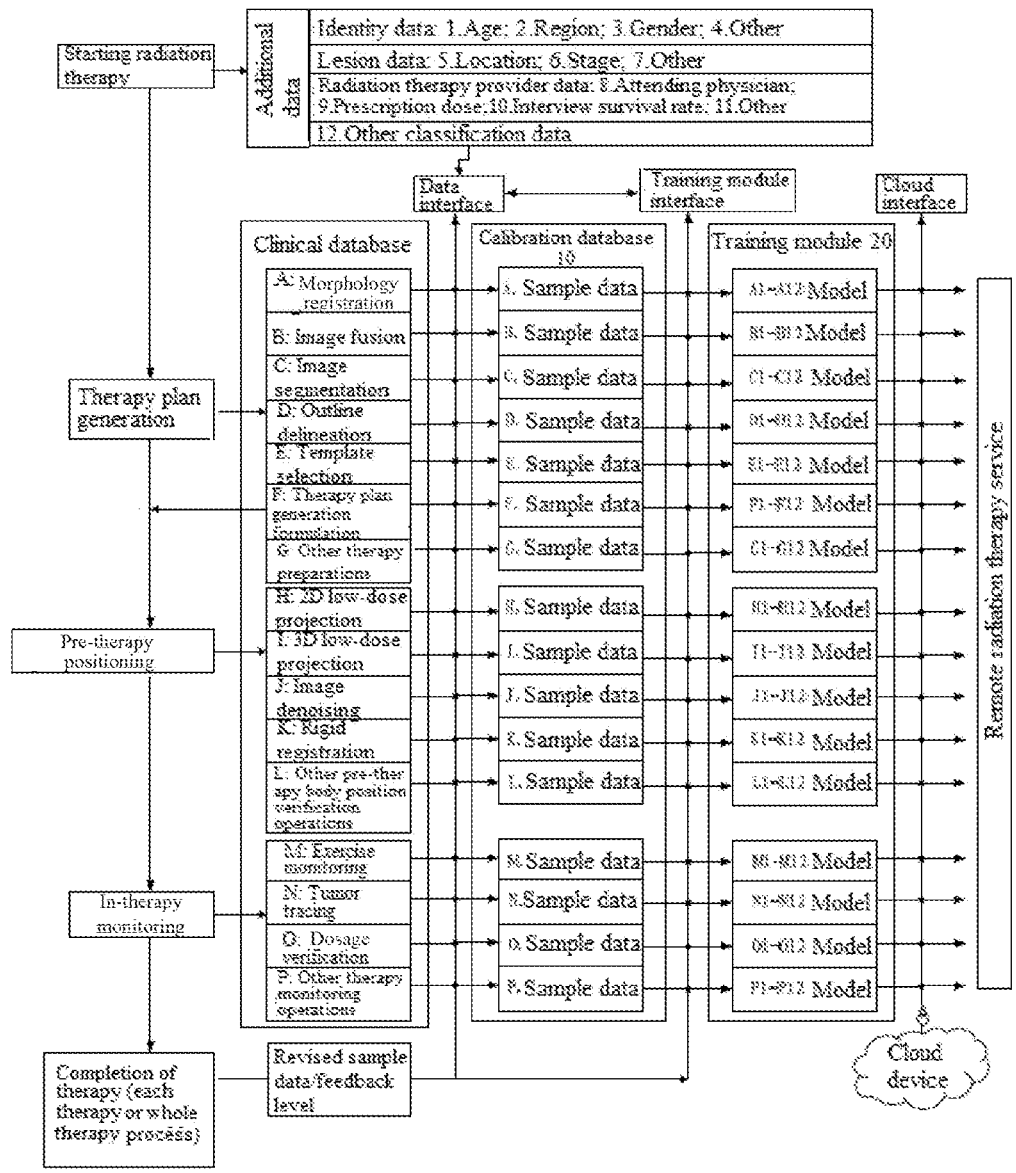
FIG. 2 is a schematic view of a structure of another radiotherapy system provided by an embodiment of the present disclosure.

FIG. 2 is a schematic view of a structure of another radiotherapy system provided by an embodiment of the present disclosure. Referring to FIG. 2, the clinical therapy process of radiotherapy generally includes a therapy plan generation stage, a pre-therapy positioning stage, an in-therapy monitoring stage, and other therapy stages, where detection data and therapy data in all stages are different. For example, at the therapy plan formulation stage, the detection data may include medical image data; and the corresponding therapy data may be a therapy plan. In the pre-therapy positioning stage, the detection data may include medical image data acquired before the therapy and in the therapy; and the corresponding therapy data may include a positioning offset of a patient. At the in-therapy monitoring stage, the detection data may include a patient displacement, a tumor monitoring image, a remaining radiation dosage, and the like during the therapy; and the corresponding therapy data may include a therapy muzzle displacement, a tumor displacement, a dosage error, and the like. In order to generate a corresponding therapy algorithm model for each therapy stage, the calibration database 10 can classify and store the sample data generated at different therapy stages. The radiotherapy system provided by the present disclosure may be applied to the entire clinical therapy process shown in FIG. 2, and may be separately applied to each stage of the clinical therapy process.

The training module 20 is used to perform deep learning on the plurality of sample data stored in the calibration database to obtain a therapy algorithm model, and send the therapy algorithm model to the data processing module 30.

The training module 20 may be connected to the calibration database 10 through a preset interface. When detecting that the amount of sample data stored in the calibration database 10 reaches a preset data amount, the training module 20 may start a deep learning on the sample data stored in the calibration database 10. For example, the deep learning may be performed through a supervised learning method, so as to obtain a therapy algorithm model.

In the embodiment of the present disclosure, as shown in FIG. 2, the training module 20 may separately perform deep learning on sample data corresponding to each therapy stage and stored in the calibration database 10, so as to obtain therapy algorithm models for each therapy stage.

It should be noted that, as the data in the clinical database is continuously updated, the sample data stored in the calibration database 10 is also continuously updated. Accordingly, the training module 20 may perform deep learning on the data stored in the calibration database 10 once detecting that the sample data in the calibration database 10 is updated, or may periodically perform deep learning on the sample data stored in the calibration database 10, so as to continuously optimize and perfect the therapy algorithm model.

The data processing module 30 is used to process the detection data acquired in the clinical therapy process according to the therapy algorithm model to generate preliminary therapy data.

In the embodiment of the present disclosure, after acquiring detection data of a patient during the clinical therapy process, the clinicians can directly input the detection data into the data processing module 30. The data processing module 30 can process the detection data according to the therapy algorithm model obtained through deep learning to generate preliminary therapy data. Since the therapy algorithm model is obtained by performing deep learning on a large amount of clinical data, the reliability of the therapy algorithm model is high. Accordingly, the accuracy of the preliminary therapy data generated through the therapy algorithm model is also high, so that the preliminary therapy data may be directly used in clinical therapy, or may be used in clinical therapy after being modified slightly by the clinicians, thereby effectively improving the therapeutic efficiency of the radiotherapy system.

Further, if the clinicians consider that the preliminary therapy data generated by the data processing module 30 is defective and cannot be used in the clinical therapy until being modified, then an operator may directly upload the modified data and the therapy data corresponding to the modified data, as modified sample data, to the calibration database 10, or may store the modified data and the corresponding therapy data in a clinical database. Then, the calibration database 10 may acquire the modified sample data from the clinical database.

After the calibration database 10 in the radiotherapy system receives the modified sample data, a weight value of the modified sample data may be set to be greater than a preset weight value by the training module 20. In addition, deep learning is again performed on the updated data in the calibration database 10.

In the embodiment of the present disclosure, when the training module 20 first trains the data stored in the calibration database 10, an initial weight value may be assigned to each sample data. The initial weight values of all sample data in the initial stage may be the same. The preset weight value may be the initial weight value. Since the modified sample data is the data modified by the clinicians, it is possible that there is a defect in an original therapy algorithm model through which the data processing module 30 generates the preliminary therapy data. Thus, the weight value of the modified sample data may be set to be relatively higher, so that when the training module 20 performs deep learning on the updated data, the impact of the modified sample data on the therapy algorithm model can be enlarged, thereby further perfecting the therapy algorithm model.

It should be noted that, in order to facilitate identification of the modified sample data by each module in the radiotherapy system, the operator may add a modification identifier to the modified sample data when storing or uploading the modified sample data. The modification identifier is used to indicate that the sample data is modified by clinicians.

In addition, if the preliminary therapy data generated by the data processing module 30 is verified by the clinicians and then directly used in clinical therapy without modification, it means that the therapy algorithm model is already relatively perfect. Therefore, there is no need to upload the therapy data and the corresponding detection data to the calibration database 10. Of course, the operator can also upload the therapy data and the corresponding detection data to the calibration database 10 to further increase the sample amount of the calibration database.

Further, in the embodiment of the present disclosure, after therapy for a patient is completed, the operator may also periodically interview the patient to follow the therapeutic effect, determine a feedback level of sample data corresponding to the patient according to the therapeutic effect, and upload the feedback level to the training module 20 in the radiotherapy system. Exemplarily, the feedback level may be positively related to the therapeutic effect. That is, the better the therapeutic effect is, the higher the feedback level is.

After receiving the feedback level of a specified sample data, the training module 20 may adjust a weight value of the specified sample data according to the feedback level of the specified sample data. The adjusted weight value of the specified sample data is positively related to the feedback level of the specified sample data. That is, the adjusted weight value of the specified sample data is positively related to the therapeutic effect thereof.

If a feedback level of specified sample data is higher, the training module 20 can determine that a therapeutic effect of therapy data in the specified sample data is better. Thus, the weight value corresponding to the specified sample data may be adjusted to be higher, so as to improve the effect of the specified sample data on the therapy algorithm model. Accordingly, if a feedback level of specified sample data is lower, the training module 20 can determine that a therapeutic effect of therapy data in the specified sample data is poorer. Thus, the weight value corresponding to the specified sample data may be adjusted to be lower, so as to reduce the effect of the specified sample data on the therapy algorithm model. If the feedback level of the specified sample data is less than a preset lower threshold, the training module 20 may set the weight value of the specified sample data to be 0, or may directly delete the specified sample data from the calibration database 10.

After the weight value of the specified sample data is adjusted, the training module 20 may perform deep learning on the sample data with the adjusted weight value in the calibration database 10, so as to continuously optimize the therapy algorithm model.

Figure 3:
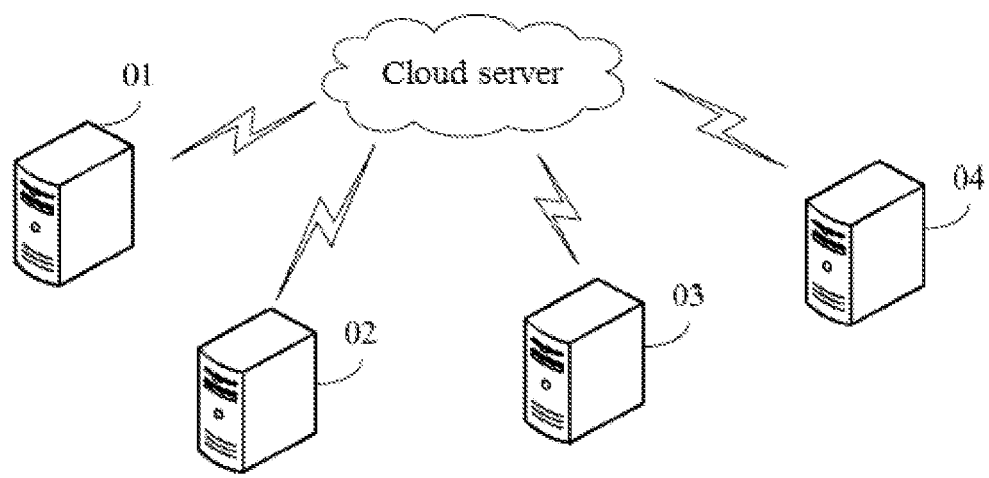
FIG. 3 is a schematic view of an application scenario of a radiotherapy system provided by an embodiment of the present disclosure.

FIG. 3 is a schematic view of an application scenario of a radiotherapy system provided by an embodiment of the present disclosure. In an implementation, the radiotherapy system may be deployed in a local server of a specified hospital, for example, may be deployed in a server 01 of a third-level and grade-A hospital. The radiotherapy system may further include a communication module. The radiotherapy system deployed in the local server 01 may upload a trained therapy algorithm model to a cloud server through the communication module, so that the cloud server can send the therapy algorithm model to local servers of other hospitals. For example, the cloud server may send the therapy algorithm model to server 02 to server 04, so that other hospitals can also acquire excellent medical resources.

In another implementation, the radiotherapy system may be deployed in a cloud server. When the radiotherapy system is deployed in the cloud server, a plurality of sample data stored in the calibration database 10 may be acquired from a clinical database of a specified hospital. Due to uneven distribution of medical levels in various regions, the medical levels of hospitals in different regions are quite different. In order to integrate excellent therapeutic resources, a provincial/municipal grade-A hospital with a higher medical level may be selected as a specified hospital. Sample data is acquired from the clinical database of the specified hospital, so as to ensure the reliability of the therapy algorithm model obtained through training.

On one hand, when the radiation therapy system is deployed in a cloud server, the radiotherapy system may further include a communication module used to send the therapy algorithm model trained by the training module 20 to a local server of any hospital, so that the local server of the any hospital can process the detection data in a clinical therapy process according to the therapy algorithm model to obtain preliminary therapy data. Herein, the any hospital may be any hospital whose server is in communication with the cloud server. The any hospital may include the specified hospital, or may also include other hospitals with a lower medical level.

Exemplarily, it is assumed that in the system shown in FIG. 3, hospitals to which the servers 01 and 02 belong are specified hospitals, the radiotherapy system deployed in the cloud server may acquire sample data from clinical databases of the servers 01 and 02 for training, so as to obtain a therapy algorithm model. Then, the radiotherapy system can send the therapy algorithm model to any one of servers 01, 02, 03 and 04 through the communication module.

On the other hand, when the radiotherapy system is deployed in a cloud server, the data processing module 30 in the radiotherapy system may also receive detection data sent from a local server of any hospital, for example, may receive detection data sent from any one of servers 01, 02, 03 and 04. Then, the data processing module 30 processes the received detection data according to the therapy algorithm model to generate preliminary therapy data, and feeds back the preliminary therapy data to the local server of the corresponding hospital.

Through the above methods, a township hospital with a lower medical level can acquire efficient remote diagnosis and therapy. The process of remote diagnosis and therapy does not require the participation of other excellent medical personnel in downtown, avoiding the disadvantages that the professional personnel have to spend time for online remote guidance. Meanwhile, the patient data security is further ensured since there is no need for the other center medical personnel to access to the patient data.

Of course, the calibration database 10 and the training module 20 in the radiotherapy system may also be deployed in the cloud server. The data processing module may be deployed in a local server of each hospital. The local server of each hospital may be in communication with the cloud server through a cloud interface, so as to acquire the therapy algorithm model trained by the training module 20. If the training module 20 optimizes the therapy algorithm model, the data processing module deployed in the local server can also upgrade the stored therapy algorithm model in real time.

Figure 4:
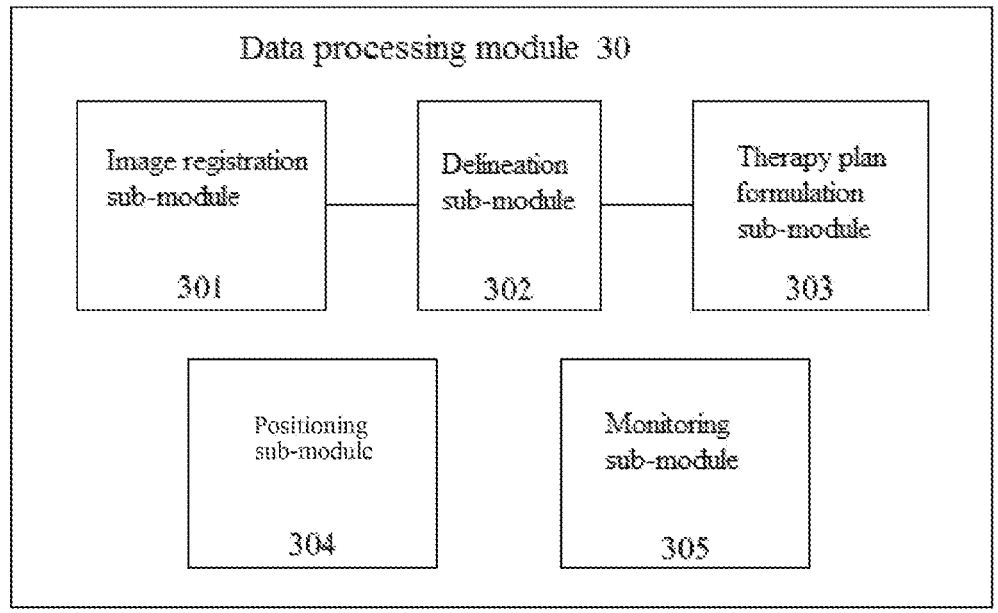
FIG. 4 is a schematic view of a structure of a data processing module provided by an embodiment of the present disclosure.

In the embodiment of the present disclosure, referring to FIG. 2, a clinical therapy process of radiotherapy may specifically include a therapy plan generation stage, a pre-therapy positioning stage and an in-therapy monitoring stage. The therapy plan generation stage may be further divided into an image registration stage, a delineation stage and a therapy plan formulation stage. In the radiotherapy system provided in the embodiment of the present disclosure, the calibration database 10 may acquire sample data of at least one stage for the training module to perform deep learning, so as to obtain a corresponding therapy algorithm model. Referring to FIG. 4, the data processing module 30 may specifically include at least one of an image registration sub-module 301, a delineation sub-module 302, a therapy plan formulation sub-module 303, a positioning sub-module 304 and a monitoring sub-module 305.

Accordingly, the training module 20 may be specifically used to execute at least one of the following methods (1)-(5), so as to obtain at least one therapy algorithm model.

(1) Deep learning is performed on a plurality of the sample data generated at the image registration stage to obtain a registration model.

In the sample data generated at the image registration stage, the detection data may be a plurality of medical image data; and the corresponding therapy data may be a registration image. Herein, the medical image data may be image data acquired through CT. MRI, etc. at different therapy stages. In this embodiment of the present disclosure, after being trained by the training module 20, the registration model may be sent to the image registration sub-module 301. The image registration sub-module 301 can process the medical image data acquired in the clinical therapy process according to the registration model, and output a preliminary registration image.

(2) Deep learning is performed on the plurality of the sample data generated at the delineation stage to obtain a delineation model.

In the sample data generated at the delineation stage, the detection data may be the registration image generated at the image registration stage; and the corresponding therapy data may be a delineation result image. A tumor area to be irradiated (i.e., a target area) and surrounding vital organs are delineated in the delineation image. In the embodiment of the present disclosure, after being trained by the training module 20, the delineation model may be sent to the delineation sub-module 302. The delineation sub-module 302 may process the registration image acquired in the clinical therapy process according to the delineation model, and output a preliminary delineation result image.

(3) Deep learning is performed on a plurality of the sample data generated in the therapy plan formulation stage to obtain a therapy plan formulation model.

In the sample data generated at the therapy plan formulation stage, the detection data may be medical image data and a delineation result image. The corresponding therapy data may be a therapy plan. The therapy plan may specifically include a radiotherapy cycle, a duration for each radiotherapy, a radiation dosage, a conformal radiotherapy of an irradiated target area, and other data. After being obtained through training by the training module 20, the therapy plan formulation model may be sent to the therapy plan formulation sub-module 303. The therapy plan formulation sub-module 303 may process the medical image data and the delineation result image acquired in the clinical therapy process according to the therapy plan formulation model, and output a preliminary therapy plan.

In addition, it should be noted that in order to ensure the reliability of the generated therapy plan, the detection data acquired in the therapy plan formulation may also include age, gender and other data related to physical conditions of a patient.

(4) Deep learning is performed on a plurality of the sample data generated at the pre-therapy positioning stage to obtain a pre-therapy positioning model.

In the sample data generated at the pre-therapy positioning stage, the detection data may include medical image data acquired at the image registration stage and medical image data acquired at the positioning stage. The corresponding therapy data may include a positioning offset. The positioning offset may refer to a offset between a current position of a patient and a target position. An operator can adjust the position of the patient according to the positioning offset, so as to ensure that radiation rays can accurately irradiate the target area. After being obtained through training by the training module 20, the positioning model may be sent to the positioning sub-module 304. The positioning sub-module 304 may process the medical image data acquired at the image registration stage and the medical image data acquired at the positioning stage during the clinical therapy process according to the positioning model, and output a preliminary positioning offset.

(5) Deep learning is performed on a plurality of the sample data generated at the in-therapy monitoring stage to obtain a monitoring model.

In the sample data generated at the therapy monitoring stage, the detection data may be the monitoring data during the therapy; and the corresponding therapy data may be adjustment data. The monitoring data may include a patient displacement, a tumor monitoring image, a remaining radiation dosage, and the like. The adjustment data may include a therapy muzzle displacement, a tumor displacement, a dosage error, and the like. Herein, the patient displacement in the monitoring data may refer to an offset of the patient position relative to the target position detected by a sensor or monitored images in a therapy process. The remaining radiation dosage may refer to the remaining amount of radiation rays after passing through a patient body detected by a detector in the therapy process. The dosage error in the adjustment data may refer to an error of the radiation dosage in the therapy plan. After being obtained through training by the training module 20, the monitoring model may be sent to the monitoring sub-module 305. The monitoring sub-module 305 may process the monitoring data acquired at the monitoring stage of the clinical therapy process according to the monitoring model, and output preliminary adjustment data.

Further, referring to FIG. 2, the image registration stage in the therapy plan generation stage may specifically include morphologic registration and image fusion. The delineation stage may specifically include image segmentation and outline delineation. The therapy plan generation stage may specifically include therapy template selection, therapy plan generation, and other therapy preparation operations. The pre-therapy positioning stage may specifically include 2D low-dose projection, 3D low-dose projection, image de-noising, rigid registration, and other pre-therapy positioning operations. The in-therapy monitoring stage may specifically include motion monitoring, tumor tracing, dosage verification, and other therapy monitoring operations. Accordingly, the calibration data 10 may store the sample data generated by each processing operation at each stage. The training module 20 may generate a therapy algorithm model for each processing operation according to the sample data corresponding to each processing operation.

In a possible implementation of the embodiment of the present disclosure, each sample data stored in the calibration data 10 may further include a set of additional data, and the additional data may include at least one piece of patient attribute information. Therefore, the impact of the above additional data is also taken into consideration in the therapy algorithm model obtained through training the sample data by the training module 20, so that the therapy algorithm model is further perfected. Accordingly, when performing clinical therapy according to the therapy algorithm model, the additional data of a patient can be input, as part of the detection data, into the therapy algorithm model.

Exemplarily, referring to FIG. 2, the set of additional data may include identity data, lesion data, therapy provider data, and other classification data of a patient. The identity data may include a plurality of patient attribute information such as gender, region, age, and the like. The lesion data may include a plurality of patient attribute information such as location and stage of a tumor, and the like. The therapy provider data may include a plurality of patient attribute information such as an attending physician, a prescription dosage, an interview survival rate, and the like.

In another possible implementation of the embodiment of the present disclosure, after the calibration database acquires the additional data in each sample data, the sample data may be further classified according to the content of target patient attribute information in the additional data of the sample data. The target patient attribute information may be pre-determined from the at least one patient attribute information. A rule for classifying the plurality of sample data may also be preset according to the content of the target patient attribute information.

Exemplarily, if the target attribute information is gender, the calibration database may classify sample data with additional data of gender being "female" into a classification, and sample data with additional data of gender being "male" into another classification in the plurality of sample data. Alternatively, if the target attribute information is age, the calibration database may classify sample data with additional data of age being below 20 years old into a classification, and sample data with additional data of age being between 20-50 years old into another classification, and sample data with additional data of age being above 50 years old into yet another classification in the plurality of sample data.

Further, the training module 20 may also perform deep learning on each classification of sample data stored in the calibration database 10 to obtain multiple classifications of therapy algorithm models.

Exemplarily, if the sample data stored in the calibration database 10 is classified into two classifications according to the gender of patients, the training module 20 may respectively perform deep learning on the two classifications of sample data, so as to obtain a therapy algorithm model for the patient attribute information of "male" and a therapy algorithm model for the patient attribute information of "female".

Accordingly, the data received by the data processing module 30 in the clinical therapy process may also include additional data corresponding to the detection data. The data processing module 30 is further used to determine a corresponding therapy algorithm model from the multiple classifications of therapy algorithm models according to the content of the target patient attribute information in the additional data, and process the received detection data according to the corresponding therapy algorithm model to generate preliminary therapy data.

Exemplarily, if the target patient attribute information is "gender" in the clinical therapy process and a gender of a patient is "female" in the additional data corresponding to the detection data received by the data processing module 30, the data processing module 30 selects the therapy algorithm model for the patient attribute information of "female" from the two classifications of the therapy algorithm models, and process the detection data according to the selected therapy algorithm model.

It should be noted that in the embodiment of the present disclosure, the calibration database 10 may also take each piece of the patient attribute information as the target attribute information in turn and perform multiple classifications on the plurality of sample data. For example, the sample data may be classified for multiple times according to patient attribute information such as age, region, gender, tumor location, and attending physician. Accordingly, the training module 20 may respectively train multiple classifications of sample data with each one corresponding to each piece of the patient attribute information, so as to obtain multiple therapy algorithm models. For example, in FIG. 2, the training module 20 may train the sample data at the morphology registration stage according to 12 pieces of the patient attribute information, such as age and region, to correspondingly obtain 12 classifications of therapy algorithm models, namely, A1-A12 models. Each therapy algorithm model may also include multiple sub-models according to different contents of the patient attribute information. Exemplarily, if the A1 model is a therapy algorithm model for the patient attribute information of age, the A1 model may specifically include a sub-model for which the patient attribute information of age is "below 20 years old", a sub-model for which the patient attribute information of age is "between 20-50 years old", and a sub-model for which the patient attribute information of age is "above 50 years old". If the A2 model is a therapy algorithm model for the patient attribute information of gender, the A2 model may specifically include a sub-model for which the patient attribute information of gender is "male" and a sub-model for which the patient attribute information of gender is "female".

In addition, the radiotherapy system provided in the embodiment of the present disclosure may also be provided with a post-intelligent module. The post-intelligent module may reduce and count sample data in the calibration dataset according to changes of various parameters of all modules in the radiotherapy system, such as, a change of sample numbers in the calibration database, adjustment of weight values of the sample data by the training module, and a change in the number of modified sample data, etc. The post-intelligent module may further inversely derive a hidden expression model of the therapy algorithm model trained by the training module.

In summary, the embodiments of the present disclosure provide a radiotherapy system. The radiotherapy system includes a calibration database, a training module and a data processing module. The calibration database can acquire a plurality of the sample data generated in a clinical therapy process. The training module can perform deep learning on the plurality of sample data stored in the calibration database to obtain a therapy algorithm model. The data processing module can process the detection data received in the clinical therapy process according to the therapy algorithm model to generate preliminary therapy data. As the therapy algorithm model is obtained through training and deep learning on a large amount of clinical data, the reliability of the therapy algorithm model is relatively higher. Accordingly, the accuracy of the preliminary therapy data generated by the therapy algorithm model is also high, so that the preliminary therapy data may be directly used in clinical therapy, or may be used in clinical therapy after being modified slightly by clinicians, thereby effectively improving the overall effectiveness of radiotherapy, as well as the therapeutic efficiency of the radiotherapy system.

Figure 5:
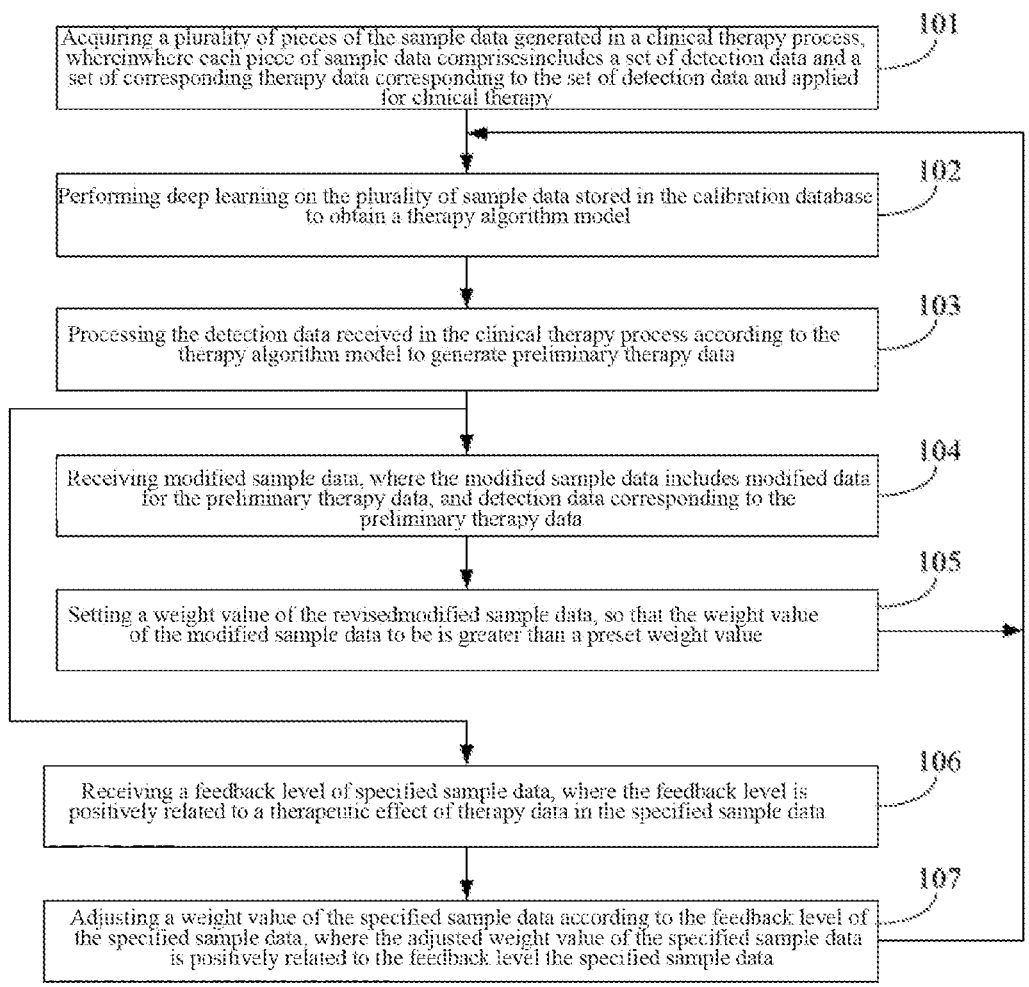
FIG. 5 is a flow chart of a data processing method provided by an embodiment of the present disclosure.

FIG. 5 is a flow chart of a data processing method provided by an embodiment of the present disclosure. The method may be applied to the radiotherapy system shown in FIG. 1 or FIG. 2. Referring to FIG. 5, the method may perform the following operations:

acquiring a plurality of sample data generated in a clinical therapy process, where each sample data includes a set of detection data and a set of therapy data corresponding to the set of detection data and applied for clinical therapy in step 101;

performing deep learning on the plurality of sample data stored in the calibration database to obtain a therapy algorithm model in step 102; and processing the detection data received in the clinical therapy process according to the therapy algorithm model to generate preliminary therapy data in step 103.

The data processing method provided by the present disclosure may be applied to the radiotherapy system shown in FIG. 1 or FIG. 2, and referring to FIG. 5, the method may further perform the following operations:

receiving modified sample data, where the modified sample data includes modified data for the preliminary therapy data, and detection data corresponding to the preliminary therapy data in step 104.

Herein, the modified data is data actually used in clinical therapy and obtained after the clinicians modifying the preliminary therapy data.

The method with reference to FIG. 5 may further perform the following operation: setting a weight value of the modified sample data to be greater than a preset weight value in step 105.

Afterwards, the radiotherapy system may execute step 102 again, i.e., may continue to perform deep learning on updated sample data in the calibration database.

As shown in FIG. 5, the data processing method provided by the present disclosure may further perform the following operations:

receiving a feedback level of specified sample data, where the feedback level is positively related to a therapeutic effect of therapy data in the specified sample data in step 106; and adjusting a weight value of the specified sample data according to the feedback level of the specified sample data, where the adjusted weight value of the specified sample data is positively related to the feedback level the specified sample data in step 107.

Afterwards, the radiotherapy system may execute step 102 again, i.e., may continue to perform deep learning on sample data with adjusted weight value.

In a possible implementation, the radiotherapy system may be deployed in a local server of a specified hospital. After obtaining the therapy algorithm model in the above step 102, the method may further perform the following operation:

sending the therapy algorithm model to a cloud server, so that the cloud server sends the therapy algorithm model to local servers of other hospitals.

In another possible implementation, the radiotherapy system may be deployed in a cloud server. The above step 101 may specifically include: acquiring multiple sets of detection data and multiple sets of therapy data corresponding to the multiple sets of detection data from a clinical database of a specified hospital. After obtaining the therapy algorithm model in the above step 102, the method may further perform the following operation: sending the therapy algorithm model to a local server of any hospital.

In yet another possible implementation, the radiotherapy system may be deployed in a cloud server. The above step 103 may specifically perform the following operations:

receiving detection data sent from a local server of any hospital in step 1031*a*; and processing the detection data according to the therapy algorithm model to generate preliminary therapy data in step 1032*a*. Further, the method may further perform the following operation:

sending the preliminary therapy data to the local server in step 1033*a*.

Optionally, in the embodiments of the present disclosure, the clinical therapy process may include at least one of: an image registration stage, a delineation stage and a therapy plan formulation stage. The sample data generated at the image registration stage may include a plurality of medical image data and a registration image corresponding to the medical image data. The sample data generated at the delineation stage includes a registration image and a corresponding delineation result image. The sample data generated at the therapy plan formulation stage includes medical image data, a delineation result image and a corresponding therapy plan.

Accordingly, the above step 102 may specifically include at least one of the following steps 1021-1023:

performing deep learning on the plurality of the sample data generated at the image registration stage to obtain a registration model in step 1021;

performing deep learning on the plurality of the sample data generated at the delineation stage to obtain a delineation model in step 1022; and performing deep learning on the plurality of the sample data generated at the therapy plan formulation stage to obtain a therapy plan formulation model.

Further, the clinical therapy process may also include a pre-therapy positioning stage and/or an in-therapy monitoring stage. The sample data generated at the pre-therapy positioning stage includes a plurality of medical image data and a corresponding positioning offset. The sample data generated at the in-therapy monitoring stage includes monitoring data and corresponding adjustment data. The monitoring data may include a patient displacement, a tumor monitoring image and a remaining radiation dosage. The adjustment data includes a therapy muzzle displacement, a tumor displacement and a dosage error.

The above step 102 may further include at least one of following steps 1024 and 1025:

performing deep learning on the plurality of the sample data generated at the pre-therapy positioning stage to obtain a pre-therapy positioning model in step 1024; and performing deep learning on the plurality of the sample data generated at the in-therapy monitoring stage to obtain a monitoring model step 1025.

In a possible implementation of the embodiment of the present disclosure, each sample data may further include a set of additional data, and the set of additional data may include at least one piece of patient attribute information. Therefore, in the above step 102, the training model obtained after the deep learning of the sample data also integrates the influence of the additional data, so that the therapy algorithm model is further perfected. Accordingly, when performing clinical therapy according to the therapy algorithm model, the additional data of a patient can be input, as part of the detection data, into the therapy algorithm model.

In a possible implementation of the embodiment of the present disclosure, each sample data may further include a set of additional data, and the set of additional data may include at least one piece of patient attribute information. After the above step 101, the method may further perform the following operation:

classifying the plurality of sample data according to the content of target patient attribute information in the additional data of each sample data, where the target patient attribute information is determined from the at least one patient attribute information.

The above step 102 may specifically include: performing deep learning on each classification of sample data stored in the calibration database to obtain multiple classifications of therapy algorithm models.

Accordingly, the data received in the clinical therapy process may also include additional data corresponding to the detection data. The above step 103 may include:

determining a corresponding therapy algorithm model from the multiple classifications of therapy algorithm models according to the content of target patient attribute information in the additional data in step 1031*b*; and processing the received detection data according to the corresponding therapy algorithm model to generate preliminary therapy data in step 1032*b*.

It should be noted that the order of the steps in the data processing method provided in the embodiments of the present disclosure may be appropriately adjusted, and the steps may also be increased or decreased according to situations. For example, steps 106 and 107 may also be executed before step 104. Changing methods that can be easily conceived by any person skilled in the art within the technical scope disclosed by the present disclosure should be covered by the protection scope of the present disclosure, and thus will not be repeated herein.

It should also be noted that in order to facilitate and simplify the description, in the above data processing method, steps 101 and 104 may be performed by the calibration database 10 in the radiotherapy system; steps 102 and 105-107 may be performed by the training module 20; and step 103 may be performed by the data processing module. The specific working process of each step may refer to the functional description of each module in the aforementioned system embodiments, and thus will not be repeated herein.

In summary, the embodiments of the present disclosure provide a data processing method. The data processing method may acquire a plurality of the sample data generated in a clinical therapy process, perform deep learning on the plurality of sample data to obtain a therapy algorithm model; and process the detection data received in the clinical therapy process according to the therapy algorithm model to generate preliminary therapy data. As the therapy algorithm model is obtained through training and deep learning on a large amount of clinical data, the reliability of the therapy algorithm model is relatively higher. Accordingly, the accuracy of the preliminary therapy data generated by the therapy algorithm model is also high, so that the preliminary therapy data may be directly used in clinical therapy, or may be used in clinical therapy after being modified slightly by clinicians, thereby effectively improving the therapeutic efficiency.

It should be understood by those skilled in the art that, all or part of the steps of the above embodiments may be implemented through hardware, or through instructions that instruct related hardware. The instructions may be stored in a computer-readable storage medium which may be any available medium that can be accessed by a computer, or may be data storage equipment such as a server and a data center integrated with one or more available media. The available medium may be a magnetic medium (for example, a floppy disk, a hard disk or a magnetic tape), an optical medium, a semiconductor medium (for example, a solid-state hard disk), or the like.

In addition, the term "and/or" in the present disclosure, which is merely used to describe association relations among associated objects, may indicate three relations. For example, "A and/or B" may indicate that A exists alone; A and B exist simultaneously; or B exists alone.

The foregoing descriptions are only exemplary embodiments of the present disclosure, and are not intended to limit the present disclosure. Any variation, equivalent substitution and modification within the spirit and principle of the present disclosure shall fall into the protection scope of the present disclosure.

What is claimed is:

1. A radiotherapy system, comprising:
a calibration database which is accessed to a clinical database through a preset database interface to acquire in real time or periodically a plurality of sample data generated in a clinical therapy process;
a training module which is connected to the calibration database through a preset interface to perform deep learning on any one of the plurality of sample data stored in the calibration database to obtain a therapy algorithm model corresponding to any one of the therapy stages, and sends the therapy algorithm model to a data processing module;
the data processing module configured to process the detection data received in the clinical therapy process according to the therapy algorithm model to generate preliminary therapy data;
wherein each sample data comprises a set of detection data and a set of therapy data corresponding to the set of the detection data and applied to the clinical therapy process and the therapy data is verified in the clinical therapy process;
the clinical therapy process comprises a therapy plan generation stage, a pre-therapy positioning stage and an in-therapy monitoring stage;
in the therapy plan generation stage, the detection data comprises medical image data, the therapy data comprises a therapy plan, and the training module is configured to perform deep learning on the detection data and the therapy data generated in the therapy plan generation stage to obtain a therapy plan formulation model;
in the pre-therapy positioning stage, the detection data comprises medical image data acquired before the clinical therapy process and in the clinical therapy process, the therapy data comprises a positioning offset of a patient, and the training module is configured to perform deep learning on the detection data and the therapy data generated in the pre-therapy positioning stage to obtain a pre-therapy positioning model;
in the in-therapy monitoring stage, the detection data comprises a patient displacement, a tumor monitoring image, a remaining radiation dosage, the therapy data comprises a tumor displacement before and after therapy, a dosage error, and the training module is configured to perform deep learning on the detection data and the therapy data generated in the in-therapy monitoring stage to obtain a monitoring model;
the calibration database classifies and stores the detection data and the therapy data generated in the therapy plan generation stage, the pre-therapy positioning stage and the in-therapy monitoring stage;
wherein:
the training module is further configured to receive a feedback level of a specified sample data, and the feedback level is positively related to a therapeutic effect of therapy data in the specified sample data; and
the training module is further configured to adjust a weight value of the specified sample data according to the feedback level of the specified sample data, wherein the adjusted weight value of the specified sample data is positively related to the feedback level of the specified sample data, and perform deep learning on sample data with the adjusted weight value in the calibration database; and
wherein:
the data processing module comprises an image registration sub-module, a delineation sub-module, a therapy plan formulation sub-module, a positioning sub-module and a monitoring sub-module;

the training module performs deep learning on a plurality of medical image data and registration images generated at an image registration stage to obtain a registration model; and the image registration sub-module processes medical image data acquired in the clinical therapy process according to the registration model and outputs a preliminary registration image;

the training module performs deep learning on the plurality of registration images and delineation result images generated at a delineation stage to obtain a delineation model; and the delineation sub-module processes registration images acquired in the clinical therapy process according to the delineation model and outputs a preliminary delineation result image;

the positioning sub-module processes the medical image data acquired at the image registration stage and the medical image data acquired at the pre-therapy positioning stage during the clinical therapy process according to the pre-therapy positioning model and outputs a preliminary positioning offset; and the monitoring sub-module processes the monitoring data acquired at the in-therapy monitoring stage of the clinical therapy process according to the monitoring model and outputs preliminary adjustment data.

2. The system of claim 1, wherein:

the calibration database is further configured to receive modified sample data, and the modified sample data comprises modified data for the preliminary therapy data, and detection data corresponding to the preliminary therapy data, wherein the modified data is the data actually used in clinical therapy and obtained after clinicians modifying the preliminary therapy data; and the training module is further configured to set a weight value of the modified sample data to be greater than a preset weight value, and perform deep learning on updated sample data in the calibration database.

3. The system of claim 1, further comprising: a communication module, wherein:

the communication module is configured to send the therapy algorithm model to a cloud server, so that the cloud server sends the therapy algorithm model to local servers of other hospitals;

or, the radiotherapy system is deployed in the cloud server, the plurality of sample data stored in the calibration database are acquired from a clinical database of a specified hospital, and the communication module is configured to send the therapy algorithm model to a local server of any hospital.

4. The system of claim 1, wherein the radiotherapy system is deployed in a cloud server; a plurality of sample data stored in the calibration database is acquired from a clinical database of a specified hospital; and the data processing module is configured to receive detection data sent from a local server of any hospital, process the detection data according to the therapy algorithm model to generate preliminary therapy data, and send the preliminary therapy data to the local server.

5. The system of claim 1, wherein:

each of the sample data further comprises a set of additional data comprising at least one patient attribute information;

the data received by the data processing module in the clinical therapy process further comprises additional data corresponding to the detection data; and the data processing module is further configured to process the received detection data and the additional data corresponding to the detection data according to the therapy algorithm model to generate the preliminary therapy data.

6. The system of claim 1, wherein:

each of the sample data further comprises a set of additional data comprising at least one patient attribute information;

the calibration database is further configured to classify the plurality of sample data according to content of target patient attribute information in the additional data of each sample data, the target patient attribute information is determined from the at least one patient attribute information;

the training module is configured to perform deep learning on each classification of sample data stored in the calibration database to obtain multiple classifications of therapy algorithm models;

the data received by the data processing module in the clinical therapy process further comprises additional data corresponding to the detection data; and the data processing module is further configured to determine a corresponding therapy algorithm model from the multiple classifications of therapy algorithm models according to the content of the target patient attribute information in the additional data, and process the received detection data according to the corresponding therapy algorithm model to generate the preliminary therapy data.

7. The system of claim 1, wherein the clinical therapy process is used to treat the patient.

8. A data processing method applied to a radiotherapy system, comprising:

acquiring, by a calibration database which is accessed to a clinical database through a preset database interface, in real time or periodically a plurality of the sample data generated in a clinical therapy process;

performing, by a training module which is connected to the calibration database through a preset interface, deep learning on any one of the plurality of sample data stored in a calibration database to obtain a therapy algorithm model, and sending the therapy algorithm model to a data processing module;

processing, by the data processing module, the detection data received in the clinical therapy process according to the therapy algorithm model to generate preliminary therapy data;

wherein each sample data comprises a set of detection data and a set of therapy data corresponding to the set of the detection data and applied to the clinical therapy process and the therapy data is verified in the clinical therapy process;

the clinical therapy process comprises a therapy plan generation stage, a pre-therapy positioning stage and an in-therapy monitoring stage;

in the therapy plan generation stage, the detection data comprises medical image data, the therapy data comprises a therapy plan, and the training module is configured to perform deep learning on the detection data and the therapy data generated in the therapy plan generation stage to obtain a therapy plan formulation model;

in the pre-therapy positioning stage, the detection data comprises medical image data acquired before the clinical therapy process and in the clinical therapy process, the therapy data comprises a positioning offset of a patient, and the training module is configured to perform deep learning on the detection data and the therapy data generated in the pre-therapy positioning stage to obtain a pre-therapy positioning model;

in the in-therapy monitoring stage, the detection data comprises a patient displacement, a tumor monitoring image, a remaining radiation dosage, the therapy data comprises a tumor displacement before and after therapy, a dosage error, and the training module is configured to perform deep learning on the detection data and the therapy data generated in the in-therapy monitoring stage to obtain a monitoring model;

the calibration database classifies and stores the detection data and the therapy data generated in the therapy plan generation stage, the pre-therapy positioning stage and the in- therapy monitoring stage;

receiving a feedback level of a specified sample data, wherein the feedback level is positively related to a therapeutic effect of therapy data in the specified sample data;

adjusting a weight value of the specified sample data according to the feedback level of the specified sample data, the adjusted weight value of the specified sample data being positively related to the feedback level of the specified sample data;

performing deep learning on sample data with the adjusted weight value; and wherein:

the data processing module comprises an image registration sub-module, a delineation sub-module, a therapy plan formulation sub-module, a positioning sub-module and a monitoring sub-module;

the training module performs deep learning on a plurality of medical image data and registration images generated at an image registration stage to obtain a registration model; and the image registration sub-module processes medical image data acquired in the clinical therapy process according to the registration model and outputs a preliminary registration image;

the training module performs deep learning on the plurality of registration images and delineation result images generated at a delineation stage to obtain a delineation model; and the delineation sub-module processes registration images acquired in the clinical therapy process according to the delineation model and outputs a preliminary delineation result image;

the positioning sub-module processes the medical image data acquired at the image registration stage and the medical image data acquired at the pre-therapy positioning stage during the clinical therapy process according to the pre-therapy positioning model and outputs a preliminary positioning offset and the monitoring sub-module processes the monitoring data acquired at the in-therapy monitoring stage of the clinical therapy process according to the monitoring model and outputs preliminary adjustment data.

9. The method of claim 8, further comprising:

receiving modified sample data, wherein the modified sample data comprises modified data for the preliminary therapy data, and detection data corresponding to the preliminary therapy data, wherein the modified data is actually used in clinical therapy and obtained after clinicians modifying the preliminary therapy data;

setting a weight value of the modified sample data to be greater than a preset weight value; and performing deep learning on updated sample data in the calibration database.

10. The method of claim 8, wherein:

after obtaining the therapy algorithm model, the method further comprises: sending the therapy algorithm model to a cloud server, so that the cloud server sends the therapy algorithm model to local servers of other hospitals;

or, the radiotherapy system is deployed in a cloud server; the acquiring the plurality of the sample data generated in the clinical therapy process comprises: acquiring the plurality of sample data from a clinical database of a specified hospital; and after obtaining the therapy algorithm model, the method further comprises: sending the therapy algorithm model to a local server of any hospital.

11. The method of claim 8, wherein the radiotherapy system is deployed in a cloud server; the acquiring the plurality of the sample data generated in the clinical therapy process comprises:

acquiring the plurality of sample data from a clinical database of a specified hospital;

the processing the detection data received in the clinical therapy process according to the therapy algorithm model to generate the preliminary therapy data comprises:

receiving detection data sent from a local server of any hospital, and processing the detection data according to the therapy algorithm model to generate the preliminary therapy data;

wherein the method further comprises: sending the preliminary therapy data to the local server.

12. The method of claim 8, wherein:

each of the sample data further comprises a set of additional data comprising at least one patient attribute information;

the data received in the clinical therapy process further comprises additional data corresponding to the detection data; and the processing the detection data received in the clinical therapy process according to the therapy algorithm model to generate the preliminary therapy data comprises:

processing the received detection data and the corresponding additional data according to the therapy algorithm model to generate the preliminary therapy data.

13. The method of claim 8, wherein:

each of the sample data further comprises a set of additional data comprising at least one patient attribute information; and the method further comprises:

classifying the plurality of sample data according to the content of target patient attribute information in the additional data of each sample data, the target patient attribute information being determined from the at least one patient attribute information;

the performing deep learning on the plurality of sample data stored in the calibration database to obtain a therapy algorithm model comprises:

performing deep learning on each classification of sample data stored in the calibration database to obtain multiple classifications of therapy algorithm models;

the data received in the clinical therapy process further comprises additional data corresponding to the detection data; and the processing the detection data received in the clinical therapy process according to the therapy algorithm model to generate the preliminary therapy data comprises:

determining a corresponding therapy algorithm model from the multiple classifications of therapy algorithm models according to the content of the target patient attribute information in the additional data; and
processing the received detection data according to the corresponding therapy algorithm model to generate the preliminary therapy data.

14. The method of claim 8, further comprising treating the patient using the clinical therapy process.

15. A non-transitory computer-readable storage medium, wherein instructions are stored in the computer-readable storage medium; and when the computer-readable storage medium runs on a computer, the computer executes a data processing method applied to a radiotherapy system, comprising:
acquiring, by a calibration database which is accessed to a clinical database through a preset database interface, in real time or periodically a plurality of the sample data generated in a clinical therapy process;
performing, by a training module which is connected to the calibration database through a preset interface, deep learning on any one of the plurality of sample data stored in a calibration database to obtain a therapy algorithm model, and sending the therapy algorithm model to a data processing module;
processing, by the data processing module, the detection data received in the clinical therapy process according to the therapy algorithm model to generate preliminary therapy data;
wherein each sample data comprises a set of detection data and a set of therapy data corresponding to the set of the detection data and applied to the clinical therapy process and the therapy data is verified in the clinical therapy;
the clinical therapy process comprises a therapy plan generation stage, a pre-therapy positioning stage and an in-therapy monitoring stage;
in the therapy plan generation stage, the detection data comprises medical image data, the therapy data comprises a therapy plan, and the training module is configured to perform deep learning on the detection data and the therapy data generated in the therapy plan generation stage to obtain a therapy plan formulation model;
in the pre-therapy positioning stage, the detection data comprises medical image data acquired before the clinical therapy process and in the clinical therapy process, the therapy data comprises a positioning offset of a patient, and the training module is configured to perform deep learning on the detection data and the therapy data generated in the pre-therapy positioning stage to obtain a pre-therapy positioning model;
in the in-therapy monitoring stage, the detection data comprises a patient displacement, a tumor monitoring image, a remaining radiation dosage, the therapy data comprises a tumor displacement before and after therapy, a dosage error, and the training module is configured to perform deep learning on the detection data and the therapy data generated in the in-therapy monitoring stage to obtain a monitoring model;
the calibration database classifies and stores the detection data and the therapy data generated in the therapy plan generation stage, the pre-therapy positioning stage and the in- therapy monitoring stage;
receiving a feedback level of a specified sample data, wherein the feedback level is positively related to a therapeutic effect of therapy data in the specified sample data;
adjusting a weight value of the specified sample data according to the feedback level of the specified sample data, the adjusted weight value of the specified sample data being positively related to the feedback level of the specified sample data;
performing deep learning on sample data with the adjusted weight value; and
wherein:
the data processing module comprises an image registration sub-module, a delineation sub-module, a therapy plan formulation sub-module, a positioning sub-module and a monitoring sub-module;
the training module performs deep learning on a plurality of medical image data and registration images generated at an image registration stage to obtain a registration model; and the image registration sub-module processes medical image data acquired in the clinical therapy process according to the registration model and outputs a preliminary registration image;
the training module performs deep learning on the plurality of registration images and delineation result images generated at a delineation stage to obtain a delineation model; and the delineation sub-module processes registration images acquired in the clinical therapy process according to the delineation model and outputs a preliminary delineation result image;
the positioning sub-module processes the medical image data acquired at the image registration stage and the medical image data acquired at the pre-therapy positioning stage during the clinical therapy process according to the pre-therapy positioning model and outputs a preliminary positioning offset and
the monitoring sub-module processes the monitoring data acquired at the in-therapy monitoring stage of the clinical therapy process according to the monitoring model and outputs preliminary adjustment data.

16. The computer-readable storage medium of claim 15, further comprising:
receiving modified sample data, wherein the modified sample data comprises modified data for the preliminary therapy data, and detection data corresponding to the preliminary therapy data, wherein the modified data is actually used in clinical therapy and obtained after clinicians modifying the preliminary therapy data;
setting a weight value of the modified sample data to be greater than a preset weight value; and
performing deep learning on updated sample data in the calibration database.

* * * * *